United States Patent [19]

Dundon et al.

[11] 4,210,601

[45] Jul. 1, 1980

[54] PROCESS FOR PREPARING ARYL[4,4'-BIS(DI-LOWERALKYL-AMINO)-BENZHYDRYL]SULFONES

[75] Inventors: John P. Dundon, North Branch; Erwin Klingsberg, Mountainside; John H. Bright, Kendall Park, all of N.J.

[73] Assignee: American Cyanamid Company, Stamford, Conn.

[21] Appl. No.: 5,251

[22] Filed: Jan. 22, 1979

[51] Int. Cl.$^2$ .............................................. C07C 85/20
[52] U.S. Cl. .................................. 260/570 D; 260/577
[58] Field of Search ..................................... 260/570 D

[56] References Cited

U.S. PATENT DOCUMENTS

| | | | |
|---|---|---|---|
| 3,193,404 | 7/1965 | Davis | 260/570 X |
| 3,373,199 | 3/1968 | Cohen et al. | 260/570 X |
| 3,557,212 | 1/1971 | Grosklos | 260/570 X |
| 3,864,400 | 2/1975 | Seibert | 260/570 |

OTHER PUBLICATIONS

Pratt et al., "Journal American Chemical Society", vol. 75, pp. 275–278 (1953).

*Primary Examiner*—Robert V. Hines
*Attorney, Agent, or Firm*—Bruce F. Jacobs

[57] ABSTRACT

Aryl[4,4'-bis(di-loweralkylamino)benzhydryl]-sulfones are prepared by reacting a 4-di(loweralkylamino)benzaldehyde with a di(loweralkyl)aniline and an aryl sulfinate.

6 Claims, No Drawings

PROCESS FOR PREPARING ARYL[4,4'-BIS(DI-LOWERALKYL-AMINO)BENZ-HYDRYL]SULFONES

The present invention relates to the preparation of aryl[4,4'-bis(di-loweralkylamino)benzhydryl]sulfone color former compounds in general and, in particular, to the preparation of p-tolyl[4,4'-bis(dimethylamino)-benzhydryl]sulfone, hereinafter referred to as PTSMH.

Aryl[4,4'-bis(di-loweralkylamino)benzhydryl]sulfones, represented by (I)

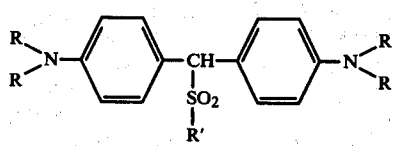

wherein each R is alkyl of 1-4 carbon atoms and R' is phenyl, naphthyl, or alkyl-, chloro-, nitro-, or alkoxy-substituted phenyl or naphthyl, have been prepared (see U.S. Pat. No. 3,864,400) by condensing the corresponding 4,4'-bis(dimethylamino)benzhydrylamine, known as "Leuco Auramine", or 4,4'-bis(diethylamino)benzhydrylamine, known as "Leuco Ethyl Auramine", in acidic solution with a sulfinic acid (II)

 (II)

The compounds are also prepared more conventionally (see Davis, U.S. Pat. No. 3,193,404) by condensing Michler's hydrol (III)

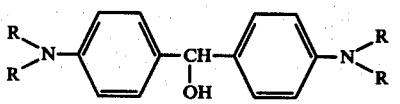

with a sulfinic acid (II) in an acidic medium, for example, glacial acetic acid.

The compounds of the invention are known color formers for the production of so-called "carbonless carbon paper" by well-known methods, as described by Davis and others. The known methods for the preparation of the compounds are not satisfactory. Michler's hydrol is an expensive intermediate, made by the reduction of the expensive precursor Michler's ketone or by the metal peroxide oxidation of the corresponding methane base. Michler's ketone is also a suspected carcinogen.

Aryl[4,4'-bis(di-loweralkylamino)benzhydryl]sulfones (I) are prepared by the condensation of an N,N-di(loweralkyl)aniline with a 4-(di-loweralkylamino)benzaldehyde and an aryl sulfinic acid in an acidic medium, optionally in the presence of urea, or by a similar process whereby the 4-(di-loweralkylamino)benzaldehyde is prepared "in situ" by reaction of an N,N-di(loweralkyl)aniline with phosphorus oxychloride and dimethyl formamide.

N,N-Di(loweralkyl)anilines, preferably N,N-dimethyl aniline, are reacted with phosphorus oxychloride in dialkyl formamide, preferably dimethyl formamide (DMF), according to the Vilsmeier Reaction to give 4-(N,N-di-loweralkylamino)benzaldehydes, preferably 4-(N,N-dimethylamino)benzaldehyde. The reaction is conducted using essentially two molar proportions of the N,N-dialkylaniline, essentially one molar proportion (or a slight excess) of phosphorus oxychloride, and essentially two molar proportions (or a slight excess) of dimethyl formamide. The phosphorus oxychloride is slowly added, with cooling, to the mixture of N,N-dialkylaniline and dimethyl formamide, keeping the temperature in the range of about 50°–70° C., preferably about 55°–65° C. The 4-(di-loweralkylamino)benzaldehyde thus formed may be isolated at this point for subsequent reaction with an N,N-di(loweralkyl)aniline and the sulfinic acid or the reaction may be continued without isolation in what is referred to herein as the "in situ" process.

During the above-described reaction, it is believed that DMF reacts with phosphorus oxychloride to form a complex (IV) which, in turn, reacts with the N,N-dialkylaniline to form another complex (V) of the aldehyde. The latter complex is decomposed by the addition of water to liberate the aldehyde. Reaction is believed to proceed as follows: (equations not balanced)

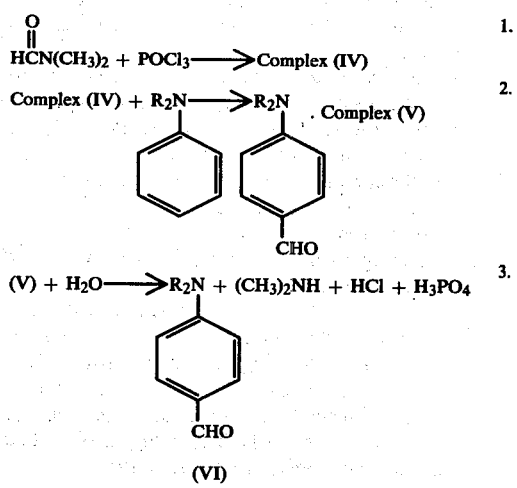

The aldehyde (VI) may be isolated at this point and reacted further with N,N-dialkylaniline and aryl sulfinic acid, as described, with or without the additional presence of urea, or the reaction may be continued by the "in situ" process, also in the presence or absence of urea.

The use of urea is optional, but better results have been obtained in its presence. Urea is believed to function to form an adduct in accordance with the following reaction sequence:

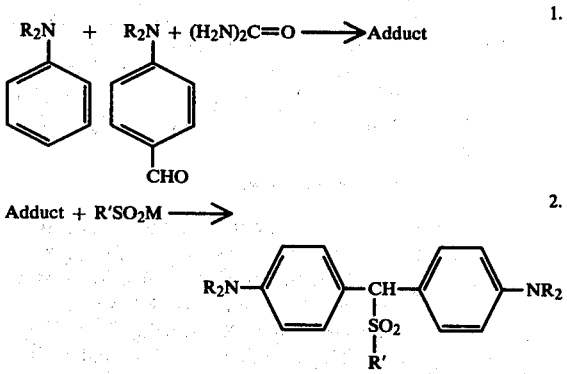

wherein R and R' are as previously defined and M is an alkali or alkaline earth metal, magnesium, ammonium or an amine salt, preferably an alkali metal.

The decomposition of the complex (V) yields some dimethylamine, hydrochloric acid and phosphoric acid. If the reaction is continued "in situ", the dimethylamine is preferably "deactivated", before proceeding, with such as either glacial acetic acid or acetic anhydride. Yields are adversely affected if the dimethylamine is not rendered "inert" to further reaction. The mechanism by which the dimethylamine affects the yield of product is not understood, but in any case its effect is reduced considerably by the addition of glacial acetic acid or acetic anhydride either prior to or following the decomposition. In general, from about 1.5 to 3 moles of acetic acid or acetic anhydride are added per mole of phosphorus oxychloride charged, preferably about 2 moles.

Following the addition of the acetic acid or acetic anhydride, the reaction mixture is rendered acidic by the addition of a strong inorganic acid, such as hydrochloric acid or sulfuric acid. The amount used will be at least enough to neutralize the aryl sulfinate (1 mole/mole of sulfinate to as much as 3 moles per mole of sulfinate).

Urea may be added at this stage. Preferably, urea is added in an amount of about one molar proportion; additional amounts have not been found to offer advantages. Then, from about 1 to 1.1 molar proportions of an alkali or alkaline earth, magnesium ammonium or amine salt of an aryl sulfinate are added.

The mixture is then heated for about 2 to about 5 hours at a temperature in the range of about 70°–95° C. It is advantageous to conduct the reaction for 2–3 hours at 90°–95° C. and then for 2–3 hours at 70°–75° C. to minimize undesired side reactions, which may occur on longer heating at the higher temperatures. It is, of course, obvious that the reaction may be conducted entirely at the lower temperatures but at a significantly slower rate. The stepwise heating program has a small, but significant, beneficial effect on yield.

The reaction mass is then drowned into a mixture of sodium hydroxide and an aromatic hydrocarbon solvent for the product, preferably toluene. Sufficient caustic soda is used to bring the pH to 5.5–7 and sufficient solvent is used to dissolve the desired product. The mixture is refluxed for a short time and then allowed to cool while the layers separate. The aqueous (brine) layer is discarded and the organic layer is washed with water. On cooling, the organic solution of product crystallizes. The crystals are filtered, washed with methanol and dried.

If the reaction is conducted by starting with the di(-loweralkylamino)benzaldehyde instead of using the "in situ" process, the reaction procedure is essentially as described except that it is not necessary to add acetic acid or acetic anhydride since no dimethylamine is present, and the acidification step requires at least 3 molar proportions of strong inorganic acid, preferably hydrochloric acid.

EXAMPLE 1

A suitable reaction vessel is charged with 2015 grams (16.65 moles) of N,N-dimethyl aniline and 1229 grams (16.83 moles) of dimethyl formamide. Phosphorus oxychloride, 1292 grams (8.44 moles), is added slowly at a rate to maintain the temperature in the range 55°–65° C. When all the phosphorus oxychloride is added, the reaction mixture is stirred at 55°–65° C. for about one hour and then cooled to 50°–60° C. Water (152 grams) is added, keeping the temperature at <60° C. during the addition. The water treatment is repeated two more times (total 456 grams); then, 3160 grams of water are added, followed by 1788 grams of hydrochloric acid (18.12 moles). The temperature increases about 10° C. Acetic anhydride (1725 grams, 16.91 moles) is added and the reaction mixture is heated to 80° C. and held for about one hour. Urea (505 grams, 8.42 moles) is added, followed by 1633 grams (9.17 moles) of sodium p-toluene sulfinate (temperature drops about 5°–10° C.). The reaction mixture is heated to 90° C., held for 2.5 hours, then drowned into a vessel containing 9888 grams of water, 5050 grams of 50% sodium hydroxide (63.13 moles) and 13,000 grams of toluene. The reaction mixture is refluxed at 90° C. for about 15 minutes and then allowed to settle for 30 minutes. The bottom (brine) layer is withdrawn and discarded. Water is added, the reaction mixture is refluxed, and the layers are again separated. This water treatment is repeated. The remaining toluene solution is cooled slowly to 30° C. and the resulting slurry is filtered, washed with methanol, and then with water. Yield is 2385 grams of product p-tolyl[4,4'-bis(dimethylamino)benzhydryl]sulfone.

EXAMPLE 2

A reaction vessel is charged with 54.7 grams of N,N-dimethyl aniline, and 33.3 grams of dimethyl formamide. Phosphorus oxychloride (35 grams) is added slowly at a rate to maintain the temperature in the range 55°–65° C. When all the phosphorus oxychloride is added, the reaction mixture is stirred at 55°–65° C. for about one hour and then cooled to 50°–60° C. Water (12.6 grams) is added in several portions, keeping the temperature at 50°–60° C. during the addition. Then, 40 ml of water are added, followed by 42 ml of 37% hydrochloric acid. Acetic acid (glacial), 50 ml, is added and the reaction mixture is heated to 80° C. and held for about one hour. Urea (13.5 grams) is added, followed by 45 grams of sodium p-toluene sulfinate. The reaction mixture is then heated to 90° C., held for 2.5 hours and drowned into a vessel containing 350 ml of toluene and 350 ml of 5 N NaOH. The reaction mixture is refluxed for about 15 minutes and the organic layer is separated from the brine layer and washed with 100 ml of water. The organic layer (450 ml) is allowed to cool and the product is filtered and dried to constant weight. There is obtained 67.6 grams of p-tolyl[4,4'-bis(dimethylamino)benzhydryl]sulfone, representing a yield of 72.4%.

When the above reaction was repeated as described, except that urea was omitted, there was obtained 16.8 grams, representing a yield of 18.0% of the product.

This example illustrates the effect of urea on the yield of the reaction.

EXAMPLE 3

N,N-Dimethyl aniline (95.8 grams) and dimethyl formamide (58.4 grams) are stirred and 61.4 grams of phosphorus oxychloride added thereto over 10 minutes. The reaction mixture is heated for 1.5 hours at 60° C., then cooled to 50° C. and 30 ml of water added over 5 minutes. Water (150 ml) and concentrated hydrochloric acid (72 ml) are added, followed by 76 ml (2.0 moles/mole of POCl$_3$) of acetic anhydride over a period of 5 minutes. The reaction mixture is heated to 75°–85° C. for 1.5 hours and then 71.6 grams of urea and 76.9 grams of sodium p-toluene sulfinate are added. The reaction mixture is then heated for 2 hours at 90° C. and added to a mixture of 600 ml of toluene and 600 ml of 5 N sodium hydroxide. The mixture is heated to 85° C. and the layers are allowed to separate. The aqueous phase is extracted with 100 ml of toluene and the organic layers combined and allowed to crystallize. There is obtained 113.8 grams of product, representing a yield of 69.7%.

When the above experiment is repeated using only 1.1 moles of acetic anhydride/mole of POCl₃, the yield of product is 33%.

EXAMPLE 4

A reaction mixture is prepared containing 31 grams "as is" (0.2 mole) of p-dimethylaminobenzaldehyde, 25 ml (0.2 mole) N,N-dimethyl aniline, 12 grams (0.2 mole) of urea, 68 ml (0.82 mole) of hydrochloric acid, 39.4 grams (0.22 mole) of 95.7% sodium p-toluene sulfinate and 117 ml of water. The mixture is heated for 3 hours at 90°-91° C. and then added to a mixture of 300 ml of hot toluene and 125 ml of 5 N sodium hydroxide. The organic layer is separated from the aqueous layer and the aqueous layer extracted twice with 50 ml of toluene. The toluene solutions are combined, refluxed, and then allowed to cool. The crystallized product is filtered and dried, yielding 75.3 grams of product p-tolyl[4,4'-bis(-dimethylamino)benzhydryl]sulfone; yield 89% based on "as is" p-dimethylaminobenzaldehyde or 92% "real".

This example illustrates the preparation of the product from isolated p-dimethylaminobenzaldehyde.

EXAMPLE 5

This example illustrates the advantage of using a step-wise heating program on the yield of the product.

N,N-Dimethyl aniline (1.18 mol) and dimethyl formamide (1.2 mol) are reacted with 0.60 mol of phosphorus oxychloride at 68°-72° C. The mixture, following addition of the phosphorus oxychloride, is warmed for 30 minutes at 60°-70° C. and then 0.61 mol of water is added in three portions, during which the temperature is reduced to 47°-48° C. Additional water (9 mol) is added at 47°-48° C., followed by 1.28 mol of concentrated hydrochloric acid and then 1.18 mol of acetic anhydride. The mixture is heated for one hour at 60°-63° C. Urea (0.60 mol), sodium p-toluenesulfinate (0.60 mol) and water (5.3 mol) are added and the mixture is heated for 2.5 hours at 85°-93° C. and the reaction quenched. The mixture is divided into three equal portions. One portion is heated for an additional 2.5 hours at 88°-90° C. and another portion is heated for an additional 2.5 hours at 65°-71° C. Following isolation of the product in the manner described in Example 1, the following results are obtained:

| Reaction Time (Hrs.) | Reaction Temperature °C. | % Real Yield |
| --- | --- | --- |
| 2.5 | 85–93 | 68.9 |
| 5 | 85–93 | 67.1 |
| 2.5 ⎫ | 85–93 ⎫ | |
| 2.5 ⎭ | 65–71 ⎭ | 71.0 |

What is claimed is:

1. A process for the preparation of aryl[4,4'-bis-(di-loweralkylamino)benzhydryl] sulfones (I)

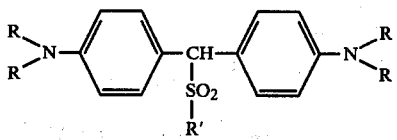

wherein each R is alkyl of 1 to 4 carbon atoms and R' is phenyl, naphthyl, alkyl-, chloro-, nitro-, or alkoxy-substituted phenyl or naphthyl, which comprises condensing, in the presence of essentially one molar proporation of urea, essentially one molar proportion of a 4-di(-loweralkylamino)benzaldehyde (II),

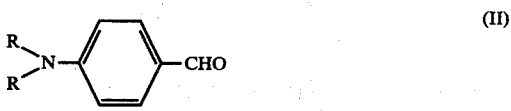

essentially one molar proportion of a di(loweralkyl)aniline (III),

and essentially one molar proportion of a salt of an aryl sulfinic acid (IV),

wherein R' is described hereinabove and M is an alkali or alkaline earth metal, magnesium, ammonium, or a salt-forming amine, in an aqueous acidic medium containing at least about 70°-95° C. for about 2 to 5 hours; adjusting the pH of the resulting reaction mixture to 5.5 to 7 by the addition of a strong inorganic base and extracting the mixture at an elevated temperature with an aromatic hydrocarbon solvent in which said (I) is soluble; separating the organic phase from the aqueous phase; and isolating said (I) from the organic phase.

2. A process in accordance with claim 1 wherein each R is methyl, R' is tolyl, M is sodium, the strong inorganic acid is hydrogen chloride, the strong inorganic base is sodium hydroxide, the aromatic hydrocarbon solvent is toluene.

3. A process for the preparation of aryl [4,4'-bis-(di-loweralkylamino)benzyhydryl]sulfones (I),

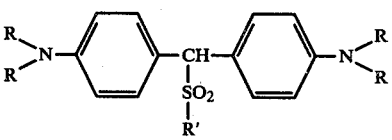

wherein each R is alkyl of 1 to 4 carbon atoms, R' is phenyl, naphthyl, alkyl-, chloro-, nitro-, or alkoxy-substituted phenyl or naphthyl, which comprises (1) forming a reaction product complex by reacting essentially two molar proportions of a di(loweralkyl)aniline (III),

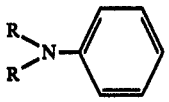

essentially two molar proportions of N,N-dialkyl formamide and essentially 1 to 1.1 molar proportions of phosphorus oxychloride at a temperature of about 50°–70° C.; (2) decomposing the reaction product complex by the addition thereto of water, thereby liberating a 4-di(loweralkylamino)benzaldehyde (II) therefrom:

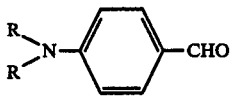

(3) acidifying the reaction mixture by the addition of about 1 to about three molar proportions of a strong inorganic acid; (4) adding thereto essentially one molar proportion of a salt of an aryl sulfinic acid (IV), $$R'-SO_2M \qquad (IV)$$

wherein R' is described hereinabove and M is an alkali or alkaline earth metal, magnesium, ammonium, or a salt-forming amine; (5) adding esentially one molar proportion of urea and heating the reaction mixture at 70°–95° C. for at least about one hour and then adjusting the pH to 5.5–7 by the addition of a strong inorganic base; (6) extracting the mixture at an elevated temperature with an aromatic hydrocarbon solvent in which said (I) is soluble and separating the resulting organic phase from the aqueous phase; and (7) isolating said (I) from said organic phase.

4. A process in accordance with claim 3 wherein about 1.5 to 3 molar proportions of glacial acetic acid or acetic anhydride are added, per mole of phosphorus oxychloride charged, prior to or following decomposition of the complex reaction product in step (2).

5. A process in accordance with claim 3 wherein each R is methyl, R' is tolyl, M is sodium, the strong inorganic acid is hydrogen chloride, the strong inorganic base is sodium hydroxide, and the aromatic hydrocarbon solvent is toluene.

6. A process in accordance with claim 3 wherein the reaction mixture is heated for about 1–2.5 hours at 90°–95° C. and then for about 1–2.5 hours at 70°–75° C. in step (5).

* * * * *